United States Patent [19]

Rubinsky

[11] Patent Number: 4,531,373
[45] Date of Patent: Jul. 30, 1985

[54] DIRECTIONAL SOLIDIFICATION FOR THE CONTROLLED FREEZING OF BIOMATERIALS

[75] Inventor: Boris Rubinsky, Berkeley, Calif.

[73] Assignee: The Regents of The University of California, Berkeley, Calif.

[21] Appl. No.: 664,164

[22] Filed: Oct. 24, 1984

[51] Int. Cl.$^3$ .............................................. F25D 13/06
[52] U.S. Cl. ............................................. 62/63; 62/65; 62/78; 62/378
[58] Field of Search .................. 62/63, 65, 78, 378, 62/380

[56] References Cited

U.S. PATENT DOCUMENTS

| | | | |
|---|---|---|---|
| 2,228,906 | 1/1941 | Bowen | 350/534 |
| 3,297,491 | 1/1967 | Kolenko | 136/204 |
| 3,580,658 | 5/1971 | Swanson | 350/93 |
| 4,030,314 | 6/1977 | Strehler et al. | 62/78 |
| 4,107,937 | 8/1978 | Chmiel | 62/64 |
| 4,117,881 | 10/1978 | Williams et al. | 62/78 |
| 4,162,677 | 7/1979 | Gregory | 62/50 |
| 4,327,799 | 5/1982 | Scheiwe et al. | 62/78 |
| 4,388,814 | 6/1983 | Schilline | 62/62 |

OTHER PUBLICATIONS

Korber et al.: "Solute Polarization During Planar Freezing of Aqueous Salt Solutions", *Int'l Journal of Heat and Mass Transfer*, May 1982, vol. 26, No. 8, pp. 1241–1253.

*Primary Examiner*—Ronald C. Capossela
*Attorney, Agent, or Firm*—Fliesler, Dubb, Meyer & Lovejoy

[57] ABSTRACT

Controlled freezing of a material (12) is accomplished by positioning an aliquot of the material (12) upon one surface (26) of a longitudinally extending substrate (14). First (30) and second (36) bases are provided each having heat transfer surfaces (32,40) which are adapted to sit in heat transfer relation with the other surface (24) of the substrate (14). The temperature of the first base (30) is controlled to be above the freezing temperature of the material (12). The temperature of the second base (36) is controlled to be below the freezing temperature of the material (12). The substrate (14) is moved longitudinally across the first base (30) in the direction of second base (36) while maintaining heat transfer relation of both bases (30,36) with the first surface (24) of the substrate (14). The frezzing rate of the material (12) is closely controlled and frozen material (12) can be produced in a continuous process.

21 Claims, 4 Drawing Figures

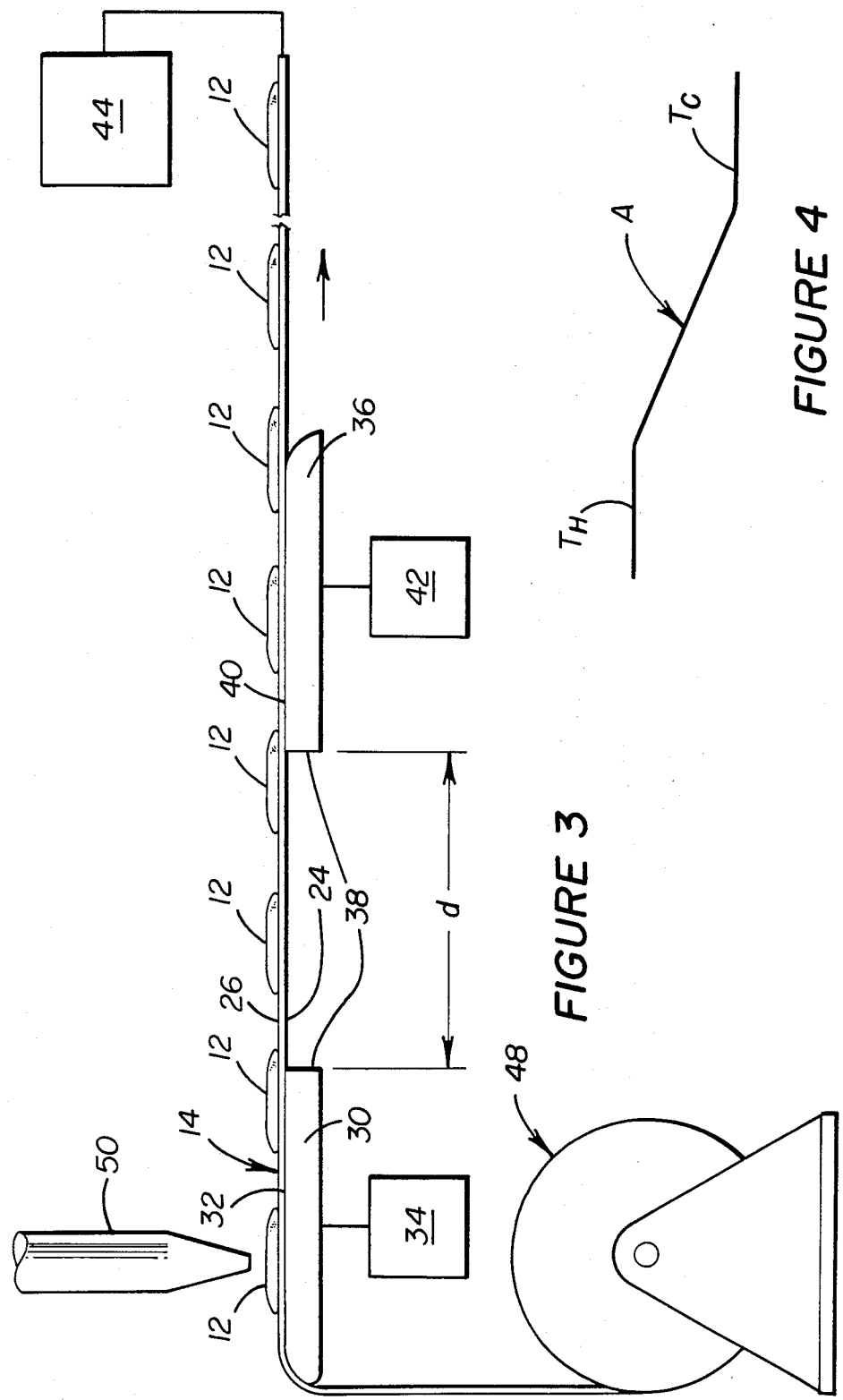

DIRECTIONAL SOLIDIFICATION FOR THE CONTROLLED FREEZING OF BIOMATERIALS

DESCRIPTION

1. Technical Field

This invention relates to a method and apparatus for freezing biomaterials such as spermatazoa, fertilized ova, and the like in a controlled manner and/or for freeze drying materials in a continuous process. Other materials may likewise be frozen. The apparatus is readily adapted for use with a microscope.

2. Background Art

Cryopreservation, the freezing of biological materials for preservation, has numerous biomedical application. The biomaterials most commonly preserved in a frozen state include red blood cells and spermatozoa (human and cattle), various cell suspension cultures and skin cultures. Currently, many researchers are trying to find methods for cryopreservation of fertilized ova and embryos and methods for the freezing of biological organs for preservation to facilitate organ transplant. There are two major types of devices for the freezing of biological material. One, is the cryomicroscope. The second is the whole sample industrial cryocooler for the freezing of various materials for commercial application.

One of the important tools of cryobiology is the cryomicroscopic system, a low temperature freezing device for application in light microscopy. The cryomicroscopic stage is commonly used to study the effects of cooling rate during freezing processes. The important effect of the cooling rate on the outcome of cryopreservation protocols is well established and the cryomicroscope has facilitated the qualitative and quantitative study of the phenomena which occur during freezing. Numerous cryomicroscopes have been developed over the years as discussed in the article "Quantitative Low Temperature Optical Microscopy Of Biological Systems, J. Microsc., Vol. 126, pages 9–28 (1982)".

In most cryomicroscopes a low temperature stage is used on which is mounted a cell suspension which is to be frozen. The stage is compatible with either transmitted or epi modes of illumination. Most cryomicroscopic stages are designed in such a way that the temperature of the sample and the stage are uniform in space and the freezing, at predetermined cooling rates, is obtained by varying in time, in a controlled mode, the uniform temperature of the stage and of the sample. The important advantage of such a design is that the physical phenomena in a specific cell can be observed continuously in time and correlated to the thermal history of the sample.

During cryopreservation with cells or whole organs the cooling rate and heating rate, rate of temperature fall and rise per unit time, during the freezing and consequent thawing processes are often the only parameters measured or controlled. The important effect of the cooling rate on the outcome of cryopreservation protocols is especially well established. Experimental evidence indicates that the relation between the cooling rate and the percentage of cells viable after a freeze-thaw cycle can be plotted as an inverse U-shaped curve, with maximal cell survival at a certain optimal rate. The survival will decrease at cooling rates either higher or lower than the optimal rate. The optimal rate varies with different cell types.

The control of the cooling rates is the most important feature of all cryomicroscopes and commercial freezing devices. All these devices try to impose a constant cooling rate during the freezing of a specimen by maintaining the temperature of the biomaterial specimen uniform in space and varying its temperature in time to obtain a constant cooling rate. Since the basic principle of this method is the maintenance of a spacially uniform temperature through the biomaterial to be frozen, the method is limited to the freezing of only small samples of biomaterials at one time. Thus, to freeze big quantities of biomaterials it is necessary to separate it into small units which must be frozen separately increasing the time and financial expenditure of the process.

It follows that a method for freezing large quantities of biomaterials (and other materials) whereby the temperature of freezing can controlled for optimal survival of the cell types being frozen and whereby essentially unlimited quantities of biomaterials can be frozen would be highly desirable. A method for freeze drying large quantities of materials in a continuous manner would also be highly desirable.

The present invention is directed to overcoming one or more of the problems as set forth above.

DISCLOSURE OF INVENTION

In accordance with an embodiment of the present invention an apparatus is provided for the controlled freezing of a material. The apparatus includes a longitudinally extending substrate having a leading edge, a trailing edge, a first surface, and a second surface, the second surface being adapted to support an aliquot of the material thereon. The apparatus further includes a first base and a second base, each having respective first and second heat transfer surfaces which are adapted to sit in heat transfer relation with the first surface of the substrate. First temperature control means serves for controlling the temperature of the first base to be above the freezing temperature of the material. Second temperature control means serves for controlling the temperature of the second base to be below the freezing temperature of the material. Moving means is provided for moving the substrate generally longitudinally across the first base in the direction of the second base with the first surface in heat transfer relation with both the first heat transfer surface and the second heat transfer surface.

In accordance with another embodiment of the present invention a method is set forth for controllably freezing a material. The method comprises positioning a longitudinally extending substrate having a leading edge, a trailing edge, a first surface and a second surface, having an aliquot of the material supported by the second surface with the first surface in heat transfer relation with first and second bases and with the bases spaced apart to define a gap therebetween. The first base is maintained at a temperature which is above the freezing temperature of the material and the second base is maintained at a temperature which is below the freezing temperature of the material. The substrate is moved longitudinally across the first base in the direction of the second base while the first and second bases are maintained in heat transfer relation with the first surface.

Utilizing an apparatus and method as set forth above, one can control the temperature of the sample being frozen in a gap between the first and second bases to have a desired cooling rate. Generally, a linear temperature gradient is created in the substrate. Freezing of the material being frozen is controlled so as to occur at a rate defined by the difference in temperature between the two bases and the velocity of the substrate. Such is useful in optical microscopy in allowing one to observe freezing phenomena utilizing a microscope. Such is also useful in cryopreservation since, as pointed out above, maximal cell survival is realized only when the rate of freezing is controlled to be optimal. Such is also useful in freeze drying since one can continuously prepare material with a high surface to volume ratio for exposure to a vacuum. Other uses include processes in which controlled solidification is required such as crystal growth for the electronic industry.

BRIEF DESCRIPTION OF DRAWINGS

The invention will be better understood by reference to the figures of the drawings wherein like numbers denote like parts throughout and wherein:

FIG. 3 illustrates an alternate embodiment of the apparatus and method of the present invention that is useful for freezing large quantities of biomaterials in a continuous manner; and FIG. 4 illustrates graphically the temperature gradient as controlled in accordance with the present invention.

BEST MODE FOR CARRYING OUT THE INVENTION

Figure 1:
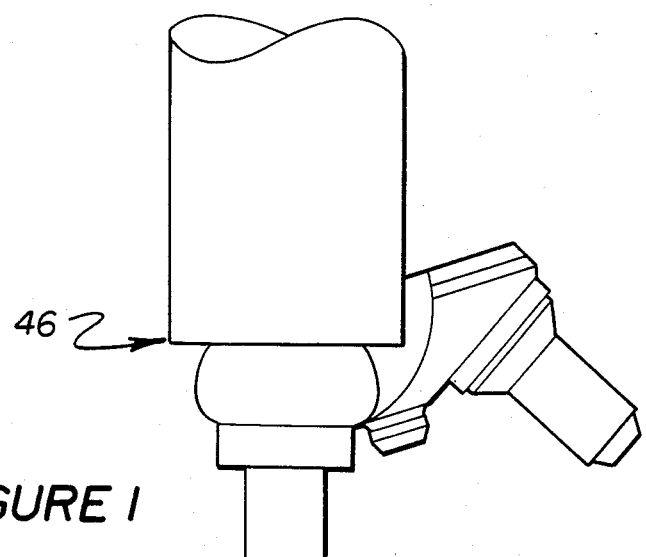
FIG. 1 illustrates, in side elevation, partially schematically, an apparatus and method in accordance with the present invention.
Figure 2:
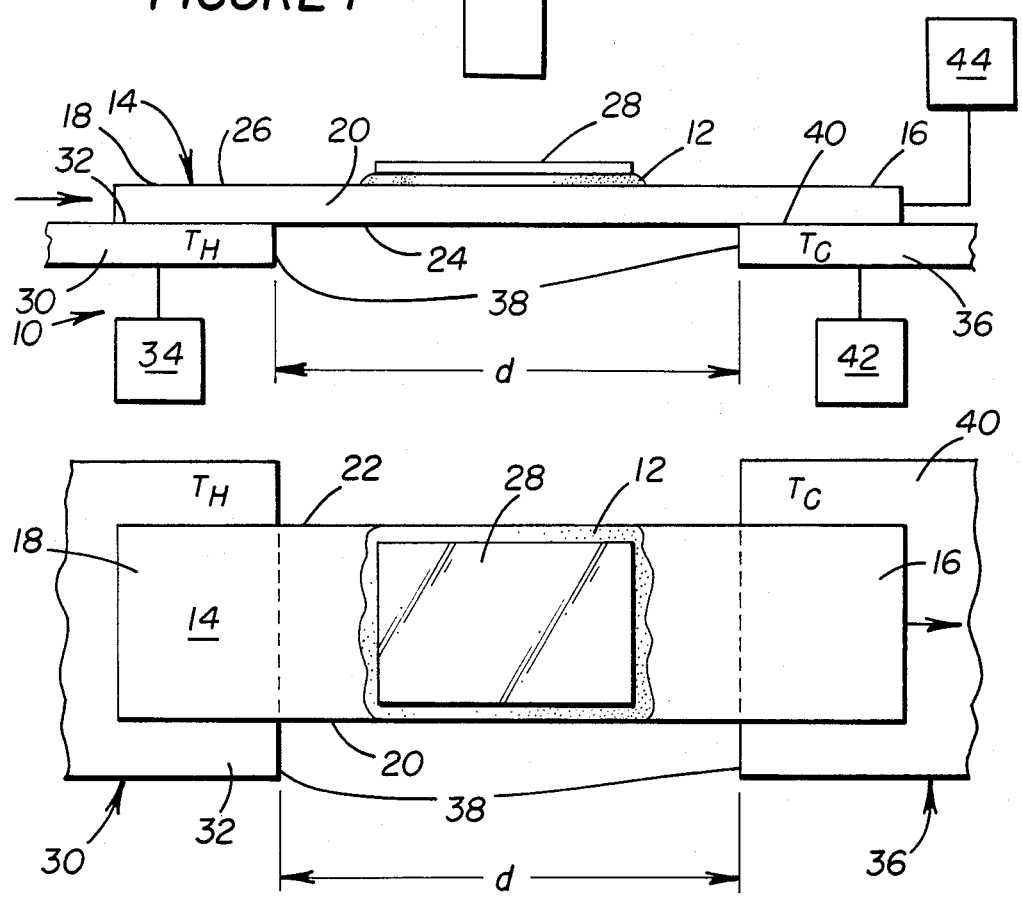
FIG. 2 illustrates, in top view, the embodiment of FIG. 1.

FIGS. 1 and 2 show an apparatus 10 in accordance with the present invention. The apparatus 10 is useful for the controlled freezing of a material 12 which, in accordance with the present invention, would normally be a biomaterial but which could alternately be a material being freeze dried, a material being crystallized, or the like. The apparatus 10, as illustrated, includes a longitudinally extending substrate 14, which, in the embodiment of FIGS. 1 and 2, comprises an ordinary microscope slide of generally constant thickness, δ.

The slide 14 has a leading end 16, a trailing end 18, a pair of lateral edge regions 20,22, a first surface 24 and a second surface 26. The second or upper surface 26 of the slide 14 is adapted to support an aliquot of the material 12 upon it. Normally, the second surface 26 will be upwardly facing and the sample 12 will simply be held there by gravity. However, it is contemplated that the actual orientation of the slide 14 is unimportant and that the sample may be supported by the second surface 26 via surface tension, through being held there with a cover slip such as the illustrated cover slip 28, or the like or by other means. An arrow in FIGS. 1 and 2 illustrates the direction of movement of the slide 14.

The apparatus 10 of the present invention includes a first base 30 having a first heat transfer surface 32 which is adapted to sit in heat transfer relation with the first surface 24 of the slide 14. First temperature control means 34 is provided for controlling the temperature, $T_H$, of the first base 30 to be a selected temperature above the freezing temperature of the material 12. Such temperature control means 34 can be of a conventional nature including, for example, a thermocouple or other heat sensing means, along with means for conducting heating and/or cooling fluids and/or with heating or cooling coils, to control the temperature of the first base 30.

A second base 36 is spaced longitudinally a distance, d, from the first base 30 to define a gap 38 therebetween. The second base 36 has a second heat transfer surface 40 which is adapted to sit in heat transfer relation with the first surface 24.

Second temperature control means 42 serves for controlling the temperature, $T_C$, of the second base 36 to be a selected temperature below the freezing temperature of the material 12. The second temperature control means 42 can be of the same nature as the first temperature control means 34. Since both are conventional in nature neither is illustrated in detail.

Moving means 44 are provided for moving the slide 14 at a selectable rate in the direction indicated by the arrow, namely, generally longitudinally across the first base 30 in the direction of the second base 36. Any convenient moving means 44 may be utilized, for example, a DC motor-gear arrangement. During the moving process the first surface 34 is maintained in heat transfer relation with both the first heat transfer surface 32 and the second heat transfer surface 40. This creates a desired temperature differential in the slide 14.

FIG. 1 illustrate an embodiment of the present invention wherein the apparatus 10 includes a microscope 46 which is positioned opposite the gap 38 and which is adapted for viewing freezing of the biomaterial 12 upon the slide 14.

FIG. 3 illustrates an alternate embodiment of the present invention. Because of the close similarity of the two embodiments identical numbers are used to depict parts which operate in an identical manner to the parts of the embodiment of FIGS. 1 and 2.

In the embodiment of FIG. 3 the substrate 14 is in the nature of a continuous strip of any desired length. The substrate 14 may be of any desired material, for example, a plastic material. The substrate 14 may be fed from a reel 48, if desired. The material 12 can be added to the strip 14 in any desired manner. In the particular embodiment illustrated, a dropper 50 is shown for delivering the biomaterial 12 onto the second surface 26 of the strip 14. The moving means 44 serves for moving the continuous strip 14 rightwardly in FIG. 3 as illustrated by the arrow. In this manner controlled freezing of the material 12 on to the second surface 26 of the strip 14 can be accomplished. Furthermore, such freezing can be at a controlled rate and can take place within the gap 38. The rate is determined by the temperature differential between that of the first base 30 and that of the second base 36 and by the rate of movement of the strip 14 in the direction of the arrow. In order to assure optimum results when freezing in this manner it may be desirable to position a microscope opposite the gap 38 and to adjust the rate of movement of the strip 14 until the freezing is occurring in the optimal manner.

It is preferred in accordance with the present invention that the temperature $T_H$, be controlled to be substantially constant and that the temperature, $T_C$, be controlled to be substantially constant. It is further preferred that the moving means 44 move the substrate 14 at substantially a constant velocity. The velocity is also generally chosen so that the temperatures of the leading end 16 is substantially equal to that of the first base 30 ($T_H$) and so that the temperature of the trailing end 18 is substantially equal to that of the second base 36 ($T_C$). Preferably the temperatures $T_H$ and $T_C$ are so chosen, and the moving means 44 moves the substrate 14 at such a velocity that the material 12 freezes when opposite the gap 38.

FIG. 4 illustrates the temperature gradient in the slide or strip 14 across the gap 38. A point labelled A in FIG. 4 corresponds to the change of phase interface in the material being frozen as the substrate 14 moves from the first base 30 towards the second base 36.

The method of the present invention is particularly useful for the controlled freezing of biomaterials. In particular, biomaterials such as red blood cells, spermatozoa, cell suspension cultures, skin cultures and fertilized ova may be readily frozen in this manner. Other materials besides biomaterials can be frozen in the same manner. Or, crystal growth may be continuously controlled in such a manner. The present invention is also particularly useful for the freezing drying of materials since it provides a controlled freezing of the materials whereby they are damaged as little as possible. The materials can then be fed into a vacuum chamber where the freeze drying is completed. Alternately, the entire apparatus, for example that of FIG. 3, can be within a vacuum chamber whereby the freezing and freeze drying can take place in a single chamber.

For optimum operation in accordance with the present invention it is important that $$\frac{h\delta}{k} << 1$$

wherein h is the heat transfer coefficient between the second surface 26 and the environment and k is the thermal conductivity of the substrate 14. When this relationship is maintained controlled freezing results and the temperature gradient is as shown in FIG. 4.

INDUSTRIAL APPLICABILITY

The present invention is particularly useful in the freezing of materials 12 such as red blood cells, spermatozoa, cell suspension cultures, skin cultures and fertilized ova. A continuous freezing process is set forth with a very great degree of control of the rate of freezing whereby minimal damage results to the biomaterials being frozen. Also, since the process can be continuous relatively large quantities of biomaterials can be readily frozen in this manner. From a scientific viewpoint, the apparatus 10 of the present invention is useful with a microscope 46 to study freezing phenomena and the effect of that phenomena upon biomaterials. In essence, freezing can be controlled to occur only along a line perpendicular to the direction of motion of a substrate 14 whereby the freezing is always properly centered under the ocular of the microscope 46.

While the invention has been described in connection with certain specific embodiments thereof other uses, advantages and objects of the invention will become apparent from a study of the foregoing specification and the accompanying drawings and the invention is intended to cover such uses, advantages and objects and is as defined in the appended claims.

I claim:

1. An apparatus (10) for the controlled freezing of a material (12), comprising:
   a longitudinally extending substrate (14) having a thickness, δ, a leading end (16), a trailing end (18), a first surface (24), and a second surface (26), said second surface 26 being adapted to support an aliquot of said material (12) thereon;
   a first base (30) having a first heat transfer surface (32) adapted to sit in heat transfer relation with said first surface (24);
   first temperature control means (34) for controlling the temperature, $T_H$, of said first base (30) to be above the freezing temperature of said material (12);
   a second base (36) spaced longitudinally a distance, d, from said first base (30) to define a gap (38) therebetween and having a second heat transfer surface (40) adapted to sit in heat transfer relation with said first surface (24);
   second temperature control means (42) for controlling the temperature, $T_C$, of said second base (36) to be below the freezing temperature of said material (12); and
   moving means (44) for moving said substrate (14) generally longitudinally across said first base (30) in the direction of said second base (36) with said first surface (24) in heat transfer relation with both said first heat transfer surface (32) and said second heat transfer surface (40).

2. An apparatus (10) as set forth in claim 1, wherein said temperature, $T_H$, is controlled to be substantially constant, said temperature, $T_C$, is controlled to be substantially constant and said moving means (44) moves said substrate (14) at substantially constant velocity.

3. An apparatus (10) as set forth in claim 2, wherein said temperatures, $T_H$ and $T_C$, are so chosen and said moving means (44) moves said substrate (14) at a velocity chosen such that said material (12) freezes when opposite said gap (38).

4. An apparatus (10) as set forth in claim 3, wherein said material (12) comprises a biomaterial (12) and said substrate (14) comprises a microscope slide and further including:
   a microscope (46) positioned opposite said gap (38) and being adapted for viewing freezing of said biomaterial (12).

5. An apparatus (10) as set forth in claim 4, wherein said biomaterial (12) is selected from the group consisting of red blood cells, spematozoa, cell suspension cultures, skin cultures and fertilized ova.

6. An apparatus (10) as set forth in claim 3, wherein said material (12) comprises a biomaterial (12) and said substrate (14) comprises a continuous strip (14).

7. An apparatus (10) as set forth in claim 6, wherein said biomaterial (12) is selected from the group consisting of red blood cells, spematozoa, cell suspension cultures, skin cultures and fertilized ova.

8. An apparatus (10) as set forth in claim 1, wherein said temperatures, $T_H$ and $T_C$, are so chosen and said moving means (44) moves said substrate (14) at a velocity chosen such that said material (12) freezes when opposite said gap (38).

9. An apparatus (10) as set forth in claim 8, wherein said material (12) comprises a biomaterial (12) and said substrate (14) comprises a microscope slide and further including:
   a microscope (46) positioned opposite said gap (38) and being adapted for viewing freezing of said biomaterial (12).

10. An apparatus (10) as set forth in claim 9, wherein said biomaterial (12) is selected from the group consisting of red blood cells, spematozoa, cell suspension cultures, skin cultures and fertilized ova.

11. An apparatus (10) as set forth in claim 8, wherein said material (12) comprises a biomaterial (12) and said substrate (14) comprises a continuous strip (14).

12. An apparatus (10) as set forth in claim 11, wherein said biomaterial (12) is selected from the group consisting of red blood cells, spermatozoa, cell suspension cultures, skin cultures and fertilized ova.

13. A method for controllably freezing a material (12) comprising:

positioning a longitudinally extending substrate (14) having a thickness, δ, a leading end (16), a trailing end (18), a first surface (24) and a second surface (26) and having an aliquot of said material (12) supported by said second surface (26) with said first surface (24) in heat transfer relation with first (30) and second (36) bases (30,36) which are spaced apart a distance, d, to define a gap (38) therebetween;

maintaining said first base (30) at a temperature, $T_H$, which is above the freezing temperature of said material (12);

maintaining said second base (36) at a temeprature, $T_C$, which is below the freezing temperature of said material (12); and moving said substrate (14) logitudinally across said first base (30) in the direction of said second base (36) while maintaining said first (30) and second (36) bases (30,36) in heat transfer relation with said first surface (24).

14. A method as set forth in claim 13, wherein said moving is at a velocity such that said material (12) freezes when opposite said gap (38).

15. A method as set forth in claim 14, wherein said temperatures, $T_H$ and $T_C$, are each maintained substantially constant.

16. A method as set forth in claim 15, wherein the velocity of which said substrate (14) is moved is maintained substantially constant.

17. A method as set forth in claim 16, wherein:

$$\frac{h\delta}{k} << 1$$

wherein
h=the heat transfer coefficient between the second surface (26) and the environment and
k=the conductivity of the substrate (14).

18. A method as set forth in claim 13, wherein said substrate (14) comprises a microscope slide (14).

19. A method as set forth in claim 13, wherein said substrate (14) comprises a continuous strip (14).

20. A method as set forth in claim 13, wherein said material (12) comprises a biomaterial (12).

21. A method as set forth in claim 20, wherein said biomaterial (12) is selected from the group consisting of red blood cells, spematozoa, cell suspension cultures, skin cultures and fertilized ova.

* * * * *